(12) United States Patent
Francois

(10) Patent No.: US 6,432,048 B1
(45) Date of Patent: Aug. 13, 2002

(54) LATERAL WALL RETRACTOR VAGINAL SPECULUM

(75) Inventor: M. Rony Francois, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 09/720,575

(22) PCT Filed: Jun. 24, 1999

(86) PCT No.: PCT/US99/14339
§ 371 (c)(1),
(2), (4) Date: Dec. 22, 2000

(87) PCT Pub. No.: WO99/66827
PCT Pub. Date: Dec. 29, 1999

Related U.S. Application Data
(60) Provisional application No. 60/090,505, filed on Jun. 24, 1998.

(51) Int. Cl.⁷ .................................................. A61B 1/32
(52) U.S. Cl. ........................................ 600/220; 600/186
(58) Field of Search ................................ 600/220, 222, 600/186, 195, 203, 207, 210, 226; 604/104, 98; 606/193

(56) References Cited
U.S. PATENT DOCUMENTS

| 2,545,201 | A | * | 3/1951 | Gilbert | ........................ 600/220 |
|---|---|---|---|---|---|
| 2,579,849 | A | | 12/1951 | Newman | |
| 3,841,317 | A | * | 10/1974 | Awais | ........................ 600/220 |
| 4,492,220 | A | | 1/1985 | Hayes | |
| 4,994,070 | A | | 2/1991 | Waters | |
| 5,007,409 | A | * | 4/1991 | Pope | ........................ 600/222 |
| 5,460,165 | A | * | 10/1995 | Mayers | ........................ 600/186 |
| 5,545,122 | A | * | 8/1996 | Spruil | ........................ 600/222 |
| 6,036,638 | A | * | 3/2000 | Nwawka | ........................ 600/186 |

FOREIGN PATENT DOCUMENTS

WO        wo-98/33431     *  8/1998    ................. 600/220

* cited by examiner

Primary Examiner—Pedro Philogene
(74) Attorney, Agent, or Firm—Anton J. Hopen; Smith & Hopen, P.A.

(57) ABSTRACT

A vaginal speculum for retaining loose vaginal tissue in a lateral direction includes a pair of blades that are moveable between an open position and a closed position. The blades in the closed position are adapted for insertion into a vagina and in the open position are adapted for dilating the vagina for providing access to a cervix. The speculum also includes a flexible membrane structure, such as a pair of membranes that extend between the blades, The membranes are adapted to retain the lateral walls of the vagina in spaced relation from a midline of the vagina when the blades are in the open position. The membranes are configured to remain in a generally collapsed configuration when the blades are in the closed position to avoid interfering with insertion or withdrawal of the speculum.

13 Claims, 4 Drawing Sheets

LATERAL WALL RETRACTOR VAGINAL SPECULUM

CROSS-REFERENCE TO RELATED APPLICATION

This application claims priority from U.S. Provisional application, Serial No. 60/090,505, filed on Jun. 24, 1998.

FIELD OF THE INVENTION

The present invention relates to a vaginal speculum and method of use, and particularly to a vaginal speculum that provides lateral wall retraction as the speculum is operated to dilate a patient's vagina.

RELATED ART

A vaginal speculum is a vital medical instrument that allows a healthcare provider to visualize the interior aspects of the vagina, as well as the distal portion of the uterus, the cervix. The speculum comprises two blades assembled together and held by a handle. The blades and the handle form a 90-degree angle. As the user holds the handle, a lever attached to the top blade allows it to open away from the inferior blade.

When the instrument is inserted into the vagina, the blades are separated in order to keep the anterior and posterior walls apart. In that position the cervix and the walls of the vagina can be seen, so long as the patient does not have excess loose vaginal tissue. Since no part of the speculum is in direct contact with the lateral walls of the vagina, the clinician tends to open the blades wider than necessary in order to keep the lateral walls apart and conduct an adequate examination. This excessive distension of the vaginal tissue remains a source of discomfort to the patient. Commonly used speculums are generally made of metal such as stainless steel and are designed to be sterilized between examinations. Disposable speculums are being used more and more frequently, particularly for convenience and decreased risk of transfer of contamination from one patient to another.

Two types of patients tend to have excess vaginal tissue: those who are multiparous and those who are obese. The multiparous patient often will have a relaxation of the levator ani musculature, which results in a tendency for the vaginal walls to collapse toward the midline during speculum examination. These muscles may be overstretched from the cumulative weight of numerous pregnancies as well as the mechanical stress of multiple vaginal deliveries.

Patients who are obese may also present this internal vaginal anatomy as a result of an increase in the amount of loose connective tissue beneath the pelvic peritoneum. When these patients have a vaginal speculum examination, the loose lateral vaginal walls similarly collapse toward the midline as the blades attempt to maintain the anterior and posterior walls apart. This collapse prevents a complete and possibly crucial visualization of the cervix for the purpose of cervical cultures, pap smears, ruptured membranes, visual assessment of a degree of dilation, and biopsy.

This problem has been addressed in the past by the combined use of two instruments, one conventional speculum and a lateral retractor having two blades facing normal those of the speculum. Such usage is suggested, for example, by literature provided by CooperSurgical, Inc. (product catalog, 1997).

This problem also has been addressed by a method known in the art of encasing the blades of a conventional speculum with a condom having its distal end removed.

Waters (U.S. Pat. No. 4,994,070) discloses a vaginal speculum that comprises a sheet member that is rolled into an elongate shape and is expandable to form a hollow tube. When expanded, the tube retains the vaginal walls away from the midline in all directions.

Hayes (U.S. Pat. No. 4,492,220) discloses a vaginal speculum that has disposable covers for the blades to prevent cross-contamination of patients examined with the same instrument.

SUMMARY OF THE INVENTION

It is thus an object of the present invention to provide a vaginal speculum, a disposable sheath for a vaginal speculum, and method of use that permits an improved visualization of the cervix in patients with excess vaginal tissue.

It is another object to provide such a speculum, sheath, and method of use that obviates the need for a second instrument to retain the lateral walls of the vagina away from the field of vision during an examination.

It is a further object to provide such a speculum, sheath, and method of use that alleviates physical discomfort experienced by a patient during a routine pelvic examination.

It is an additional object to provide such a speculum, sheath, and method of use that, while retaining the lateral walls, also permits visualization of the lateral walls.

Another object is to provide such a speculum, sheath, and method of use that, while retaining the lateral walls, also permits access to the lateral walls.

A further object is to provide a disposable sheath for use with a currently available nondisposable or disposable speculum, and a method of use therefor that includes a currently available instrument having a sheath added thereto.

These and other objects of the present invention are achieved by the present invention, a lateral wall retractor vaginal speculum, sheath, and method of use. The speculum comprises a pair of blades that are movable between an open position and a closed position. The blades in the closed position ire adapted for insertion into a vagina; in the open position the blades are adapted for dilating the vagina for providing access to a cervix.

The speculum further comprises a flexible membrane structure that extends between the blades. This membrane structure is adapted to retain the lateral walls of the vagina in spaced relation from a midline of the vagina when the blades are in the open position.

The speculum also comprises means for retaining the membrane structure in a generally collapsed configuration when the blades are in the closed position. This feature permits generally unobstructed insertion and withdrawal and minimizes a risk of pinching excess tissue upon closing the blades within the vagina.

In a particular embodiment, the membrane structure comprises a sheath, which comprises a tubular member having a pair of distal pockets. The pockets are of appropriate dimensions to cover the distal ends of the blades of a speculum. The sheath when placed on a speculum provides for retention of the lateral walls of the vagina in spaced relation from a midline of the vagina when the blades of the speculum are in the open position. The pockets prevent the sheath from being pushed in a proximal direction toward the handle of the speculum during insertion into the vagina.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

DETAILED DESCRIPTION OF THE PREFERRED EMBODIMENTS

A description of the preferred embodiments of the present invention will now be undertaken with reference to FIGS. 1–7.

In all preferred embodiments of the present invention the speculum includes two generally opposed blades movable between a closed position for insertion and withdrawal and an open position for performing a pelvic examination. The blades each have a pair of lateral edges, an outer surface, and an inner surface facing that of the opposing blade. The blades are each attached to a downwardly depending handle, which operate in cooperation to effect blade movement. Typically a locking mechanism is provided for locking the blades in a desired position.

A flexible membrane structure extends between the blades for retaining the lateral walls of the vagina in spaced relation from a midline of the vagina when the blades are in the open position. During a vaginal examination, the membrane structure becomes apposed to the lateral walls of the vagina and prevent excess tissue from collapsing toward the midline, which would result in the visual obstruction of the cervix. This achieves the object of reducing patient discomfort by obviating the need for opening the blades more widely to keep the lateral walls apart.

The speculum also comprises means for retaining the membrane structure in a generally collapsed configuration when the blades are in the closed position. The speculum may be disposable; alternatively the speculum may be made of materials suitable for sterilization between uses.

Figure 1:
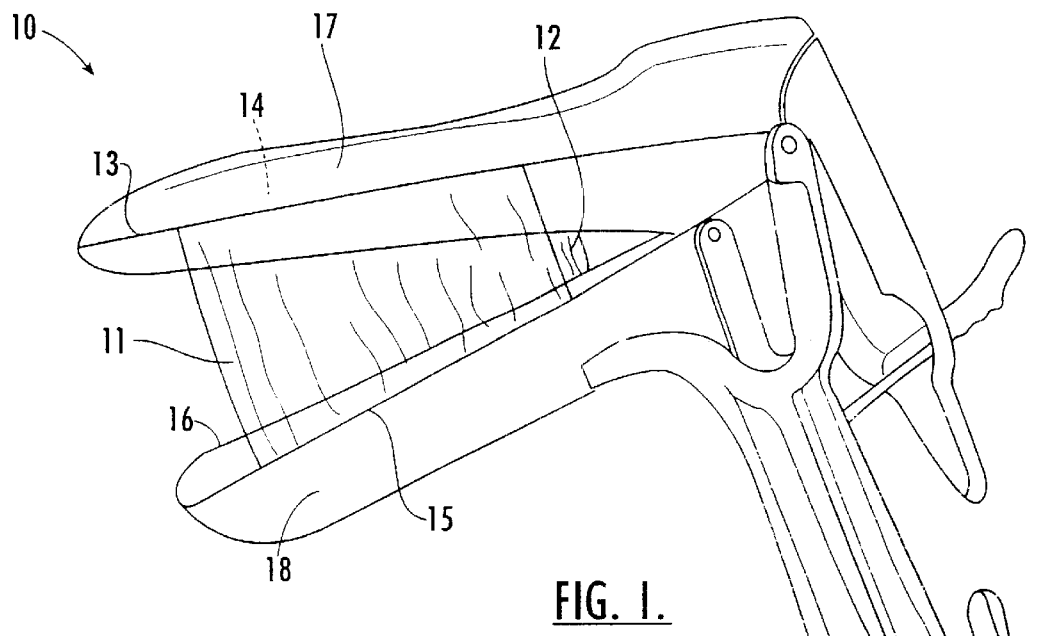
FIG. 1 is a perspective view of a first embodiment of the invention, a disposable vaginal speculum having a membrane linking the superior and inferior blades.
Figure 2:
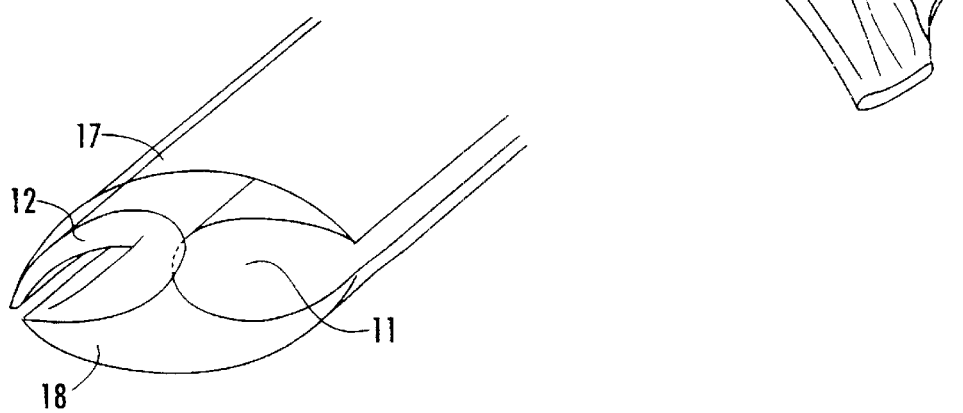
FIG. 2 is a closeup view of the distal end of the embodiment illustrated in FIG. 1.

A first embodiment is illustrated in FIGS. 1 and 2, wherein the speculum 10 comprises a disposable unit having a pair of transparent plastic membranes 11,12 affixed to and linking the lateral edges 13,14 and 15,16 of the upper 17 and lower 18 blades, respectively. This affixing of the membranes 11,12 to the blades' lateral edges 13,14 and 15,16 may be accomplished in any of a number of ways, such as, but not limited to: heat sealing them together; using a nontoxic adhesive; using ultrasound; cementing with solvent; and applying sufficient pressure that adherence occurs.

In FIG. 2 the blades 17,18 are in the closed position, and the membranes 11,12 are seen in a folded configuration to which they are biased, wherein they will not interfere with insertion or withdrawal.

Figure 3:
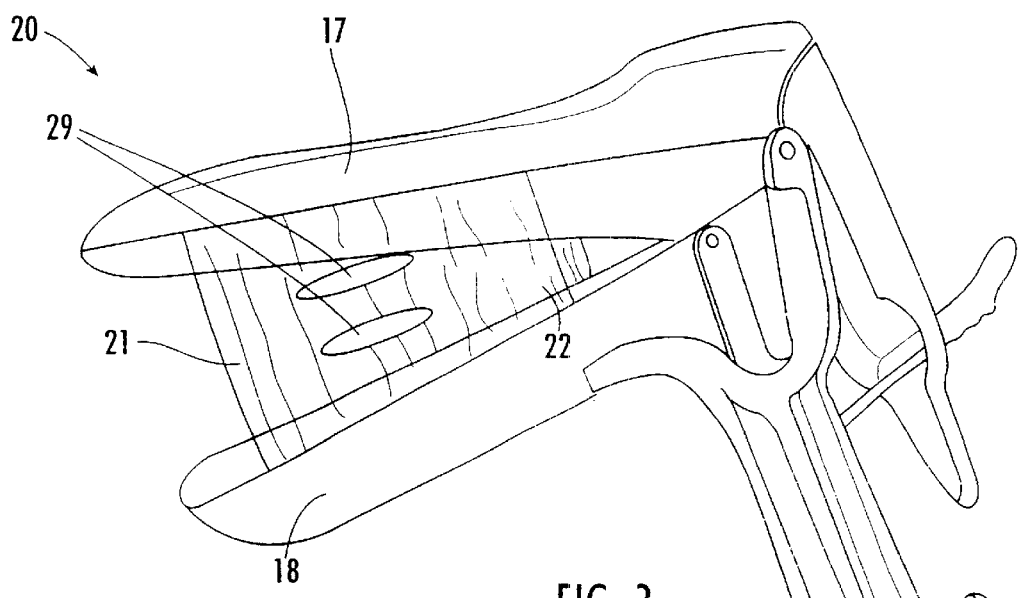
FIG. 3 is a perspective view of a second embodiment of the invention, a disposable vaginal speculum having a membrane linking the superior and inferior blades, the membrane having fenestrations therein.

A second embodiment is illustrated in FIG. 3, wherein the speculum 20 is essentially identical to that 10 of the first embodiment, with a difference that a plurality of fenestrations 29 are formed in the membranes 21,22 through which access may be gained to the lateral walls for, for example, performing a biopsy of a suspicious area.

Figure 4:
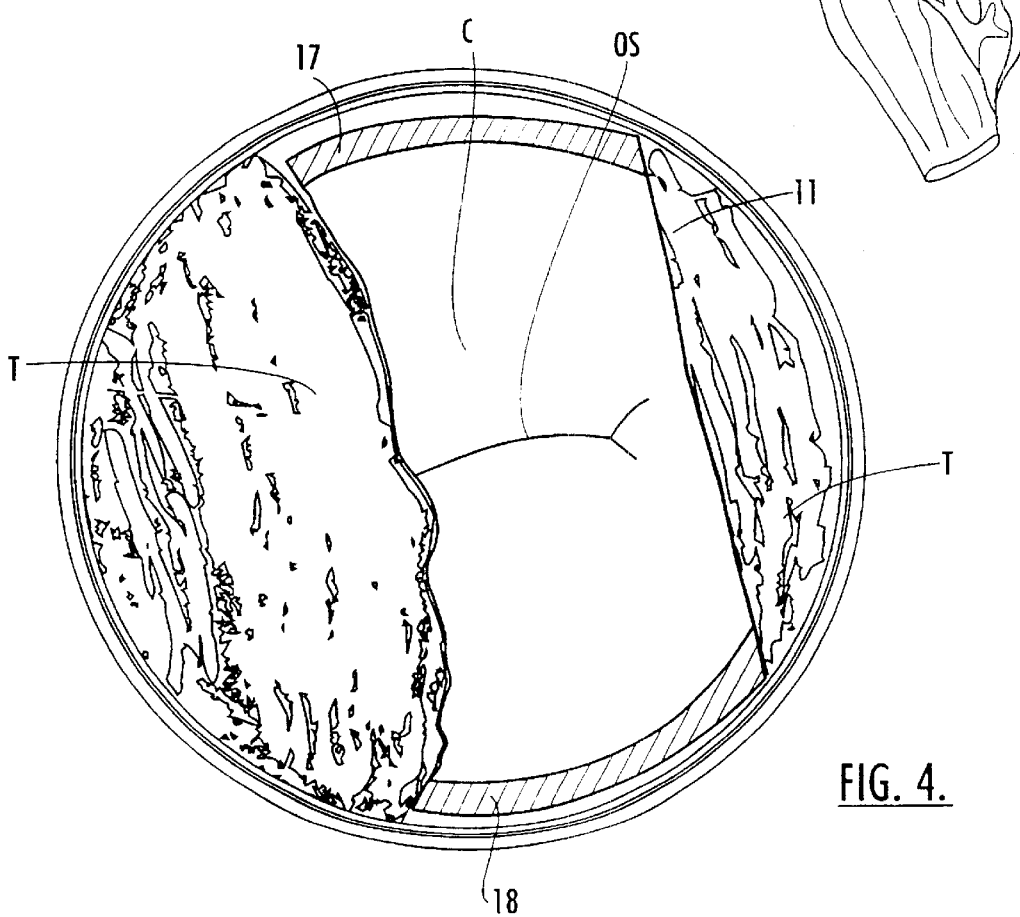
FIG. 4 is a transverse view of a speculum inside a vagina, illustrating an inadequate visualization of the cervix with a conventional speculum (left side) and an improved view as provided by the present invention (right side).

The effect of the present invention is illustrated in FIG. 4, wherein the left side of the drawing indicates a perspective during a conventional vaginal speculum examination, showing inadequate visualization of the cervix C, owing to protrusion of loose lateral tissue T into the field. Such a problem could result in missed pathological cervical lesions. The right side, on the other hand, illustrates a perspective during an examination using one of the specula of the present invention. As the plastic membrane 11 retracts the loose tissue T, excellent visualization of the cervix C is permitted, allowing cervical cultures, pap smears, and biopsies to be effectively performed.

Figure 5:
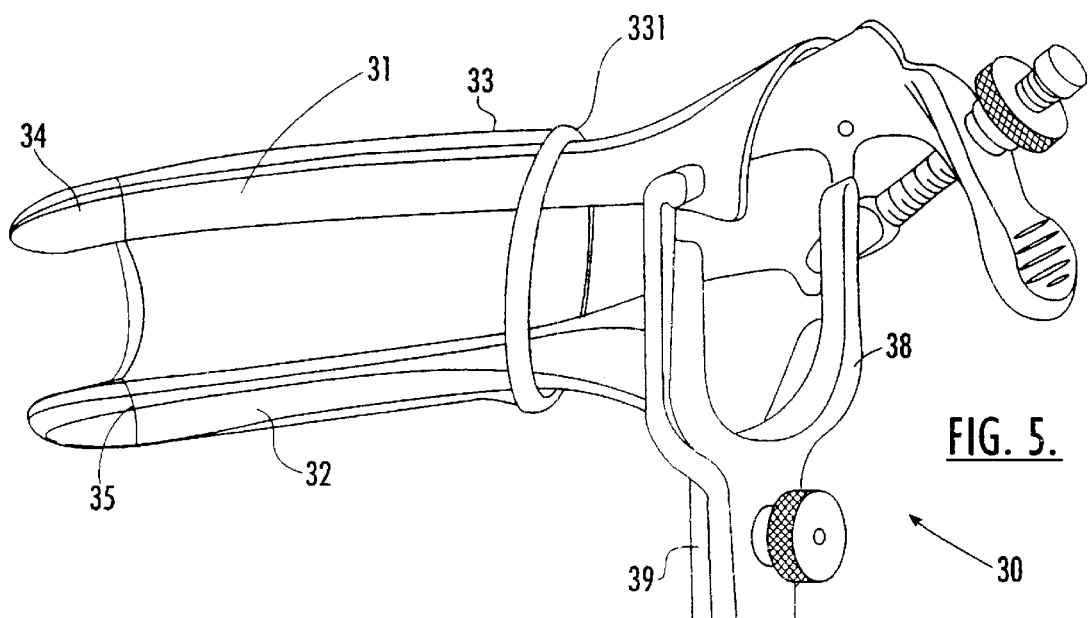
FIG. 5 is a perspective view of a third embodiment of the invention, a reusable speculum having a disposable sheath placed over the blades.
Figure 6:
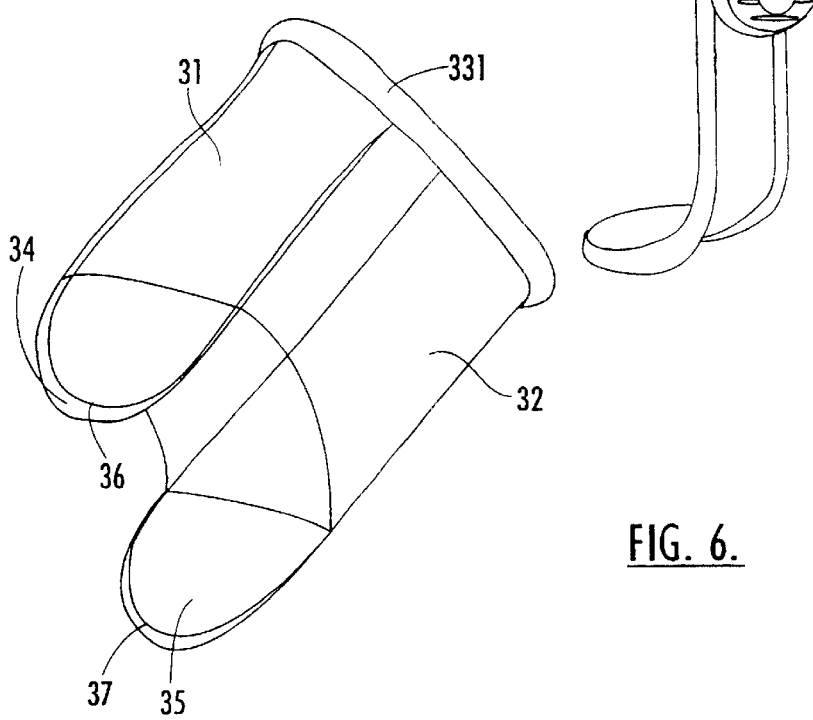
FIG. 6 is a closeup view of the distal end of the embodiment illustrated in FIG. 5.

A third embodiment, illustrated in FIGS. 5 and 6, comprises a sheath of appropriate dimensions to fit over a conventional speculum 30, such as a metal reusable speculum known in the art, the sheath providing modifications to achieve the objects of the present invention. In this embodiment the sheath substantially covers the blades 31,32 and comprises a disposable tubular member 33 that has a pair of distal pockets 34,35. Each of these pockets 34,35 is dimensioned to receive a distal end 36,37 of one of the blades 31,32. These pockets 34,35 prevent the tubular member 33 from being pushed in a proximal direction toward the handles 38,39. Preferably the tubular member 33 has a length sufficient so that its proximal end 331 protrudes outside the vagina during the examination, so that the inserted portions of the blades 31,32 are covered throughout.

Figure 7:
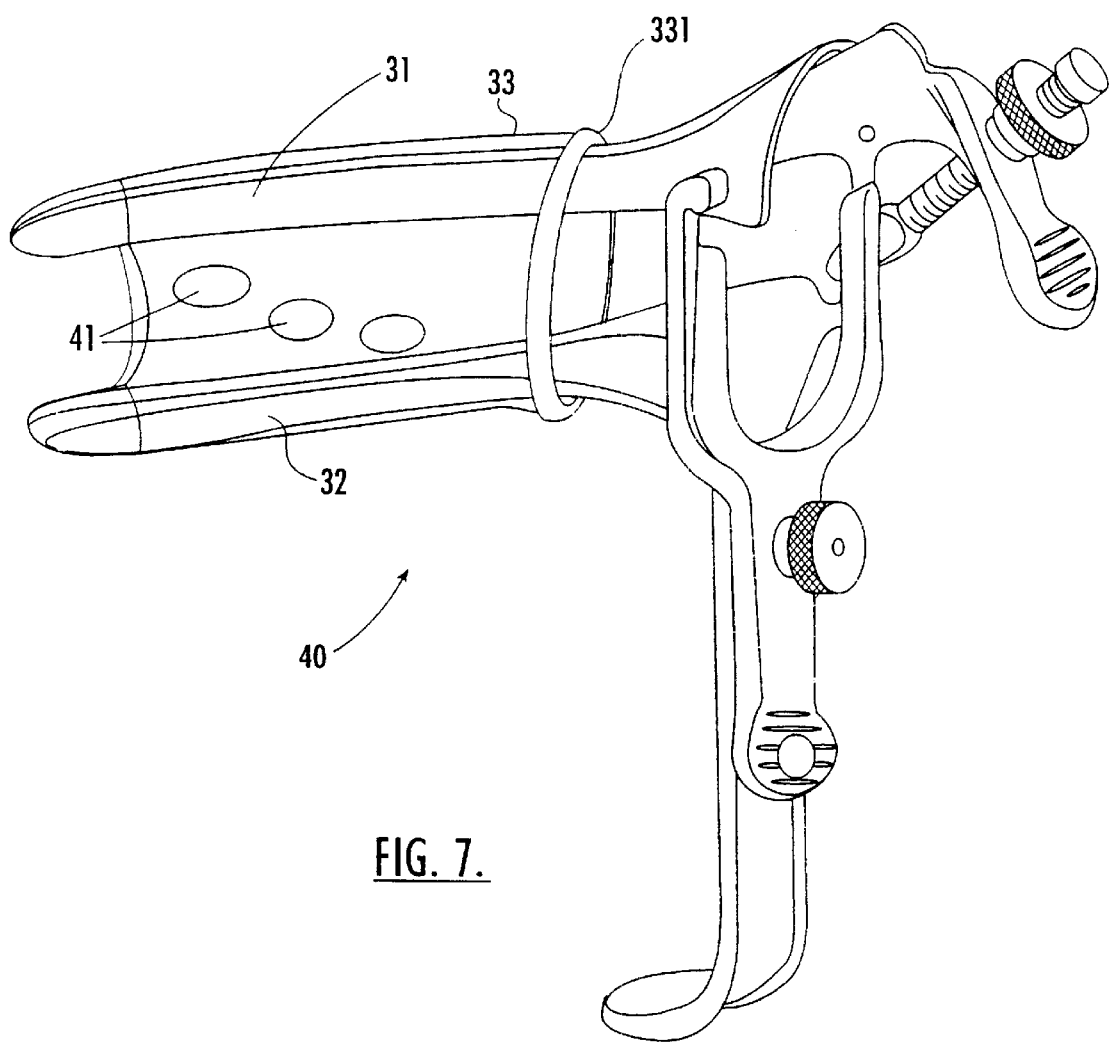
FIG. 7 is a perspective view of a fourth embodiment of the invention, a reusable speculum having a disposable sheath placed over the blades, the sheath having fenestrations therein.

The fourth embodiment, illustrated in FIG. 7, in similar fashion to the second embodiment, comprises a sheath 40 substantially identical to the third embodiment 33, 34, 35, with the addition of membrane fenestrations 41 to the tubular member 43.

It may be appreciated by one skilled in the art that additional embodiments may be contemplated.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus illustrated and described herein are by way of example, and the scope of the invention is not limited to the exact details of construction or use.

Having now described the invention, the construction, the operation and use of preferred embodiment thereof, and the advantageous new and useful results obtained thereby, the new and useful constructions, and reasonable mechanical equivalents thereof obvious to those skilled in the art, are set forth in the appended claims.

What is claimed is:

1. A vaginal speculum comprising:

a pair of blades, movable between an open position and a closed position, the blades in the closed position adapted for insertion into a vagina and in the open position adapted for dilating the vagina for providing access to a cervix;

a flexible membrane structure affixed to and extending between lateral edges of the blades, the membrane structure adapted to unfold in a substantially lateral plane responsive to the blades moving to the open position whereby the lateral walls of the vagina are retained in spaced relation from a midline of the vagina and the membrane structure inwardly collapsing responsive to the blades moving to the closed position whereby the membrane structure does not project outward from the lateral edges of the blades and thus will not interfere with insertion or withdrawal of the pair of blades.

2. The speculum recited in claim 1, wherein the membrane structure comprises a pair of membranes affixed to and extending in substantially parallel fashion between the lateral edges of each blade, the membrane structures adapted to unfold in substantially planar orientations responsive to the blades moving to the open position whereby the lateral walls of the vagina are retained in spaced relation and the pair of membranes inwardly collapsing responsive to the blades moving to the closed position whereby the pair of membranes will not interfere with the insertion or withdrawal of the pair of blades.

3. The speculum recited in claim 2, wherein at least one of the membranes has at least one laterally oriented fenestration therein for providing access to a lateral wall of the vagina.

4. The speculum recited in claim 1, wherein the membrane structure comprises a tubular member having a pair of distal pockets integral therewith, each pocket dimensioned to receive a distal end of one of the blades.

5. The speculum recited in claim 1, further comprising a pair of downwardly depending handle members, one handle member affixed to each of the blades, the handle members operable in cooperation to move the blades between the open and the closed position.

6. The speculum recited in claim 5, wherein the handle members are relatively lockable for maintaining a desired position therebetween.

7. The speculum recited in claim 1, wherein the speculum is disposable.

8. The speculum recited in claim 1, wherein the membrane structure comprises a transparent material.

9. A sheath for a vagina speculum comprising:

a flexible membrane tubular member for covering opposed blades of a speculum, the tubular membrane adapted to unfold in a substantially lateral plane responsive to the blades moving to an open position to retain lateral walls of a vagina in spaced relation from a midline of the vagina, the tubular member inwardly collapsing responsive to the blades moving to a closed position whereby the tubular member does not project outward from lateral edges of the blades and thus will not interfere with insertion or withdrawal of the pair of blades; and a pair of distal pockets integral with the tubular member, each pocket dimensioned to receive a distal end of a speculum blade.

10. The sheath recited in claim 9, wherein the sheath is disposable.

11. The sheath recited in claim 9 wherein the membrane comprises a pair of membranes affixed to and extending in substantially parallel fashion between the lateral edges of each blade, the membrane structures adapted to unfold in substantially planar orientations responsive to the blades moving to the open position whereby the lateral walls of the vagina are retained in spaced relation and the pair of membranes inwardly collapsing responsive to the blades moving to the closed position whereby the pair of membranes will not interfere wit the insertion or withdrawal of the pair of blades.

12. The sheath recited in claim 11, wherein the pair of membranes comprise transparent material.

13. The sheath recited in claim 11, wherein at least one of the pair of membranes has at least one laterally oriented fenestration therein for providing access to a lateral wall of the vagina.

\* \* \* \* \*